United States Patent [19]

Delaney et al.

[11] Patent Number: 4,798,904
[45] Date of Patent: Jan. 17, 1989

[54] CERTAIN [(LOWER ALKANOYL-THIO)METHYL-1-OXO-3-PHENYL PROPYL AMINO]BENZENE LOWER ALKANOIC ACID OR ESTER DERIVATIVES WHICH INHIBIT ENKEPHALINASE

[75] Inventors: Norma G. Delaney, Princeton; Eric M. Gordon, Pennington; Miguel A. Ondetti, Princeton, all of N.J.

[73] Assignee: E. R. Squibb & Sons, Inc., Princeton, N.J.

[21] Appl. No.: 119,930

[22] Filed: Nov. 13, 1987

Related U.S. Application Data

[60] Division of Ser. No. 896,318, Aug. 13, 1986, Pat. No. 4,722,810, which is a continuation of Ser. No. 641,221, Aug. 15, 1984, abandoned, which is a continuation-in-part of Ser. No. 538,731, Oct. 3, 1983, abandoned.

[51] Int. Cl.⁴ .......................................... C07C 153/11
[52] U.S. Cl. ................................................ 558/254
[58] Field of Search .................................... 558/254

[56] References Cited

U.S. PATENT DOCUMENTS

| | | |
|---|---|---|
| 4,053,651 | 10/1977 | Ondetti et al. ............... 558/254 |
| 4,105,776 | 8/1978 | Ondetti et al. ............... 558/254 |
| 4,199,512 | 4/1980 | Ondetti et al. ............... 558/254 |
| 4,216,160 | 8/1980 | Dorn et al. .................... 558/254 |
| 4,235,885 | 11/1980 | Sundeen et al. ............... 558/254 |
| 4,297,275 | 10/1981 | Sundeen et al. ............... 558/254 |
| 4,327,111 | 4/1982 | Sundeen et al. ............... 558/254 |
| 4,329,363 | 5/1982 | Dorn et al. .................... 558/254 |
| 4,339,600 | 7/1982 | Ondetti et al. ............... 558/254 |
| 4,401,677 | 8/1983 | Greenberg et al. ............ 558/254 |
| 4,513,009 | 4/1985 | Roques et al. ................ 558/254 |
| 4,610,816 | 9/1986 | Berger ......................... 558/254 |

FOREIGN PATENT DOCUMENTS

0038758 7/1981 European Pat. Off. ........... 558/254
0054862 10/1982 European Pat. Off. ........... 558/254

OTHER PUBLICATIONS

Patey et al., "Selective Protection . . . Enkephalinase Inhibition," Science, vol. 212, pp. 1153–1155, 1981.
Ondetti et al., "Bradykinin Analogs Containing β-Homoamino Acids," J. Med. Chem., vol. 18, pp. 761–763, 1975.
Cushman et al., "Design of Potent . . . Amino Acids", Biochemistry, vol. 16, pp. 5484–5491, 1977.
Mumford et al., "Inhibition of . . . Dipeptides," Biochemical and Biophysical Res. Comm., vol. 109, pp. 1303–1309, 1982.
Hughes et al., "Identification . . . Agonist Activity", Nature, vol. 258, pp. 577–579, 1975.
Malfroy et al., "High-Affinity . . . after Morphine," Nature, vol. 276, pp. 523–526, 1978.
Roques et al., "The Enkephalinase Inhibitor . . . in Mice," Nature, vol. 288, pp. 286–288, 1980.

*Primary Examiner*—Alan L. Rotman
*Assistant Examiner*—Robert C. Whittenbaugh
*Attorney, Agent, or Firm*—Lawrence S. Levinson; Stephen B. Davis

[57] ABSTRACT

Acylmercaptoalkanoyl compounds of the formula

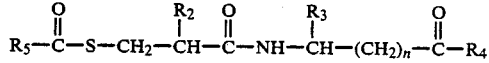

wherein n is an integer from one to fifteen possess enkephalinase inhibition activity and are useful as analgesic agents.

17 Claims, No Drawings

CERTAIN [(LOWER ALKANOYL-THIO)METHYL-1-OXO-3-PHENYL PROPYL AMINO]BENZENE LOWER ALKANOIC ACID OR ESTER DERIVATIVES WHICH INHIBIT ENKEPHALINASE

RELATED APPLICATIONS

This application is a division of application Ser. No. 896,318 filed Aug. 13, 1986, now U.S. Pat. No. 4,722,810, which was a continuation of application Ser. No. 641,221, filed on Aug. 15, 1984, now abandoned, which was a continuation-in-part of application Ser. No. 538,731 filed Oct. 3, 1983, now abandoned.

BACKGROUND OF THE INVENTION

Greenberg et al. in U.S. Pat. No. 4,401,677 disclose that various mercaptoalkanoyl α-amino acids are useful analgesic agents due to their enkephalinase inhibition activity.

Ondetti et al. in U.S. Pat. No. 4,053,651 disclose that various mercaptoalkanoyl and acylmercaptoalkanoyl α-aminoacids are useful hypotensive agents due to their angiotensin converting enzyme inhibition activity.

Roques et al. (Nature, Vol. 288, Nov. 1980, p.286–288) disclose that thiorphan, [(D,L)-3-mercapto-2-benzylpropanoyl]-glycine, is an inhibitor of enkephalinase in vitro in nanomolar concentration and in vivo after either intracerebroventricular or systemic administration.

Roques et al. in European Patent Application No. 38,758 disclose various α-amino acid derivatives including mercaptoalkanoyl and acylmercaptoalkanoyl derivatives as possessing enkephalinase inhibition activity.

Mumford et al. (Biochemical And Biophysical Research Comm., vol. 109, No. 4, 1982, p. 1303–1309) disclose that various substituted N-carboxymethyl dipeptides including those having a terminal β-alanine group possess enkephalinase inhibition activity.

Berger et al. in European Patent Application No. 54,862 disclose enkephalinase inhibiting peptides of the formula

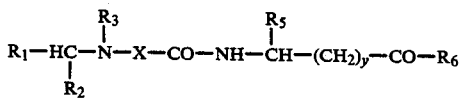

wherein $R_2$ is a carboxylic or phosphonic acid or ester and y is zero or an integer from 1 to 3.

Cushman et al. (Biochemistry, Vol. 16, No. 25, 1977, p. 5484–5491) disclose various carboxyalkanoyl and mercaptoalkanoyl amino acids as angiotensin converting enzyme inhibitors. Among the compounds disclosed is

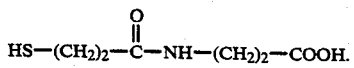

Sundeen et al. in U.S. Pat. Nos. 4,235,885 and 4,297,275 disclose mammalian collagenase inhibitors including mercaptoalkanoyl and acylmercaptoalkanoyl compounds of the formula

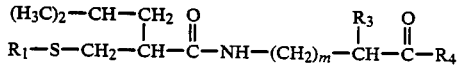

wherein m is zero or an integer from 1 to 9, $R_3$ includes hydrogen, and $R_4$ includes hydroxy and amino.

Sundeen et al. in U.S. Pat. No. 4,327,111 disclose mammalian collagenase inhibitors including mercaptoalkanoyl and acylmercaptoalkanoyl compounds of the formula

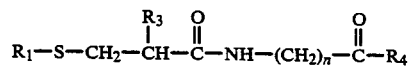

wherein $R_4$ is hydrogen, alkyl or aryl, n is an integer from 1 to 20, and $R_3$ is alkyl of 3 to 8 carbons, cycloalkyl of 3 to 7 carbons, aryl, or arylalkyl.

SUMMARY OF THE INVENTION

This invention is directed to the use of the mercaptoalkanoyl and acylmercaptoalkanoyl compounds of formula I and salts thereof as analgesic agents (I)

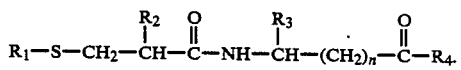

$R_1$ is hydrogen or

$R_2$ is lower alkyl,

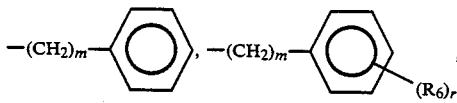

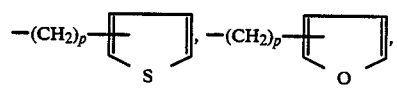

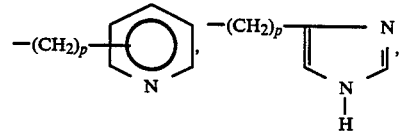

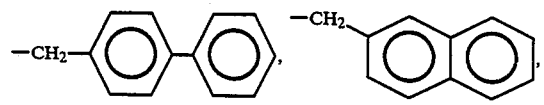

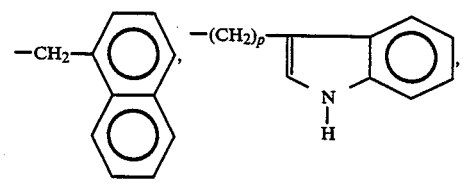

or —$(CH_2)_p$-cycloalkyl.

$R_3$ is hydrogen, lower alkyl,

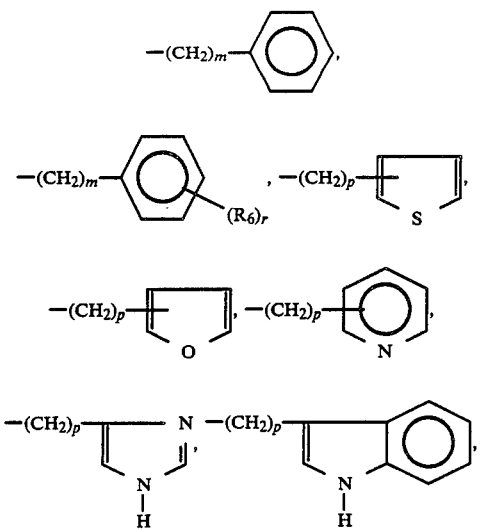

or —$(CH_2)_p$-cycloalkyl.

$R_4$ is hydroxy, lower alkoxy,

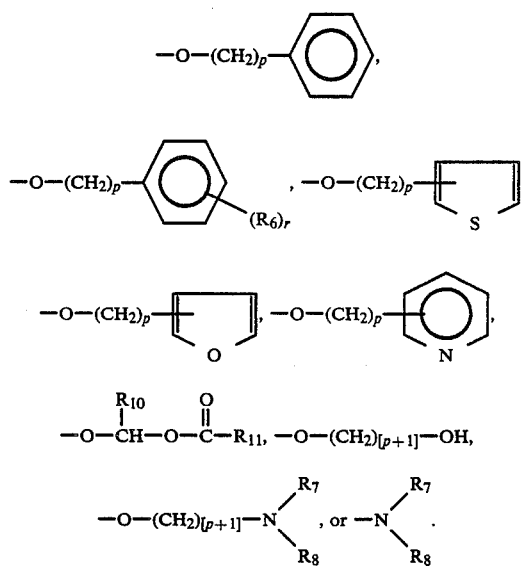

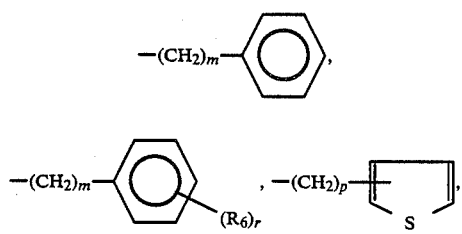

$R_{10}$ is hydrogen, lower alkyl, cycloalkyl, or phenyl.
$R_{11}$ is hydrogen, lower alkyl, lower alkoxy, or phenyl.
n is an integer from 1 to 15.
$R_5$ is lower alkyl,

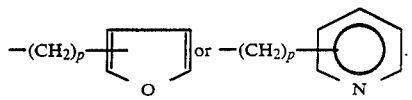

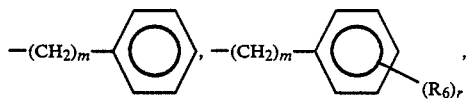

p is an integer from 1 to 4.
m is zero or an integer from 1 to 4.
$R_6$ is lower alkyl of 1 to 4 carbons, lower alkoxy of 1 to 4 carbons, lower alkylthio of 1 to 4 carbons, hydroxy, Cl, Br, F, amino, —NH-lower alkyl of 1 to 4 carbons, —N(lower alkyl)$_2$ wherein lower alkyl is of 1 to 4 carbons, nitro or trifluoromethyl.

r is an integer from 1 to 3 provided that r is more than one only if $R_6$ is hydroxy, methyl, methoxy, Cl, or F.

$R_7$ and $R_8$ are independently selected from the group consisting of hydrogen, lower alkyl,

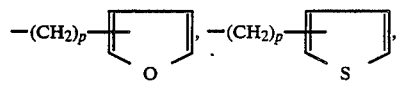

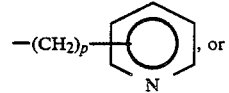

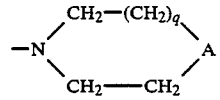

$R_7$ and $R_8$ join together with the N-atom to form a ring of the formula

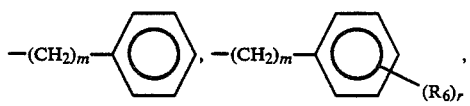

wherein q is zero or one, A is CH—$R_9$, oxygen, or N-$R_9$, and $R_9$ is hydrogen or lower alkyl of 1 to 4 carbons.

This invention is also directed to the novel compounds of formula I wherein $R_1$, $R_3$, $R_4$, n, $R_5$, m, p, $R_6$, r, $R_7$ and $R_8$ are as defined above and $R_2$ is

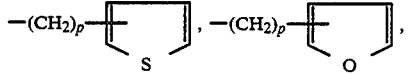

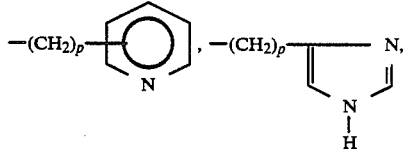

-continued

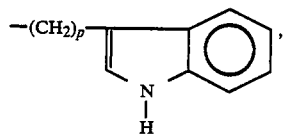

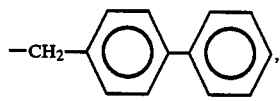

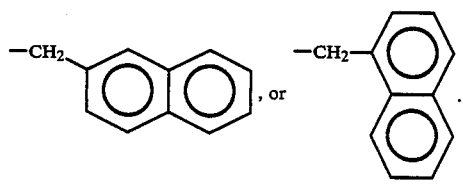

DETAILED DESCRIPTION OF THE INVENTION

The term lower alkyl used in defining various symbols refers to straight or branched chain hydrocarbon radicals having up to seven carbons, for example, methyl, ethyl, propyl, isopropyl, isobutyl, butyl, t-butyl, pentyl, isopentyl, etc. The preferred lower alkyl groups are up to four carbon atoms with methyl and ethyl most preferred. Similarly, the terms lower alkoxy and lower alkylthio refer to such groups attached to an oxygen or sulfur.

The term cycloalkyl refers to saturated rings of 3 to 7 carbons, preferably cyclopentyl, cyclohexyl, and cycloheptyl.

The symbols $$-(CH_2)_p-\left[\begin{array}{c}\\S\end{array}\right], -(CH_2)_p-\left[\begin{array}{c}\\O\end{array}\right], \text{ and}$$

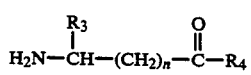

represent that the alkylene bridge is attached to an available carbon atom.

The compounds of formula I can be prepared by acylating an amino compound of the formula (II)

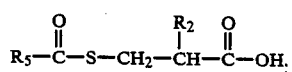

with an acid or its chemical equivalent of the formula (III)

$$R_5-\overset{O}{\overset{\|}{C}}-S-CH_2-\overset{R_2}{\overset{|}{C}H}-\overset{O}{\overset{\|}{C}}-OH.$$

The above acylation yields the acylmercaptoalkanoyl compounds of formula I, i.e., $R_1$ is

Treatment of these acylmercaptoalkanoyl compounds by conventional hydrolysis yields the corresponding mercaptoalkanoyl compounds of formula I, i.e., $R_1$ is hydrogen.

This acylation reaction can be effected in the presence of a coupling agent such as dicyclohexylcarbodiimide or the like, or the acid of formula III can be activated by formation of its mixed anhydride, symmetrical anhydride, acid halide, active ester or the use of Woodward reagent K, n-ethoxycarbonyl-2-ethoxy-1,2-dihydroquinoline or the like. For a review of the methods of acylation, see Methoden der Organischen Chemie (Houben-Weyl), Vol. XV, part II, page 1 et seq. (1974). Preferably, the acid halide, especially the acid chloride, of formula III is employed.

The products of formula I wherein $R_1$ is hydrogen and $R_4$ is lower alkoxy or the various substituted lower alkoxy groups can be prepared by treating the compound of formula I wherein $R_1$ is

and $R_4$ is hydroxy with the appropriate alcohol in the presence of dicyclohexylcarbodiimide and dimethylaminopyridine followed by selective saponification.

The products of formula I wherein $R_1$ is

and $R_4$ is hydroxy can be prepared by acylation of the corresponding compound of formula I wherein $R_1$ is hydrogen and $R_4$ is hydroxy with the appropriate acyl halide.

The compounds of formula I wherein $R_4$ is

can be prepared by employing the amino compound of formula II with the amide group in place. Alternatively, when $R_7$ and $R_8$ are hydrogen the intermediate of formula II can be employed as a carboxylic acid ester, i.e., $R_4$ is lower alkoxy, and following completion of the acylation reaction, the acylmercaptoalkanoyl amino acid is treated with a methanolic solution of ammonia. When $R_7$ and $R_8$ are not both hydrogen, the compound of formula I wherein $R_1$ is

and $R_4$ is hydroxy can be reacted with an amine of the formula (IV)

$$HN\begin{matrix}R_7\\\\R_8\end{matrix}$$

in the presence of dicyclohexylcarbodiimide. The $$R_5-\overset{O}{\underset{\|}{C}}-$$

can then be removed by hydrolysis as described above to yield the compounds of formula I wherein $R_1$ is hydrogen.

The ester products of formula I wherein $R_4$ is $$-O-\underset{\underset{R_{10}}{|}}{CH}-O-\overset{O}{\underset{\|}{C}}-R_{11}$$

can be prepared by employing the amino compound of formula II in the above reactions with the ester group already in place. Alternatively, the product of formula I wherein $R_4$ is hydroxy and $R_1$ is $$R_5-\overset{O}{\underset{\|}{C}}-$$

can be treated with a molar equivalent of the compound of the formula (V)

$$L-\underset{\underset{R_{10}}{|}}{CH}-O-\overset{O}{\underset{\|}{C}}-R_{11}$$

wherein L is a leaving group such as chlorine, bromine, tolylsulfonyl, etc. The $$R_5-\overset{O}{\underset{\|}{C}}-$$

group can then be removed by selective saponification to yield the products wherein $R_1$ is hydrogen.

The amino intermediates of formula II are known in the art or can be prepared from the known α-amino acids by successive homologations following the procedure described by Ondetti et al. (Journal of Medicinal Chemistry, 1975, Vol. 18, No. 7, pages 761–763).

The acylmercapto carboxylic acid intermediates of formula III are prepared according to the procedures described in various patent and literature references, as note, for example, Ondetti et al., U.S. Pat. Nos. 4,053,651 and 4,105,776, and Sundeen U.S. Pat. Nos. 4,235,885 and 4,327,111.

Preferred compounds of formula I are those wherein:
$R_1$ is hydrogen, $$H_3C-\overset{O}{\underset{\|}{C}}-, \text{ or } \underset{\bigcirc}{}-\overset{O}{\underset{\|}{C}}-,$$

especially hydrogen.

$R_2$ is $$-(CH_2)_m-\bigcirc, \quad -(CH_2)_m-\bigcirc-R_6,$$

$$-CH_2-\underset{S}{\square}, \quad -CH_2-\underset{O}{\square}, \quad -CH_2-\underset{N}{\bigcirc},$$

$$-CH_2-\underset{\underset{H}{N}}{\square}-N \text{ or } -CH_2-\underset{\underset{H}{N}}{\bigcirc}$$

wherein m is one or two and $R_6$ is methyl, methoxy, Cl, F, amino, nitro, or hydroxy, especially benzyl.

$R_3$ is hydrogen, straight or branched chain lower alkyl of 1 to 4 carbons $$-(CH_2)_m-\bigcirc, \quad -(CH_2)_m-\bigcirc-R_6,$$

$$-CH_2-\underset{S}{\square}, \quad -CH_2-\underset{O}{\square}, \quad -CH_2-\underset{N}{\bigcirc},$$

$$-CH_2-\underset{\underset{H}{N}}{\square}-N, \text{ or } -CH_2-\underset{\underset{H}{N}}{\bigcirc}$$

wherein m is one or two and $R_6$ is methyl, methoxy, Cl, F, hydroxy, amino, or nitro.

$R_4$ is hydroxy, methoxy, $-NH_2$, $$-O-\underset{\underset{R_{10}}{|}}{CH}-O-\overset{O}{\underset{\|}{C}}-R_{11}$$

wherein $R_{10}$ is hydrogen, straight or branched chain lower alkyl of 1 to 4 carbons or cyclohexyl and $R_{11}$ is straight or branched chain lower alkyl of 1 to 4 carbons, especially wherein $R_4$ is hydroxy.

n is an integer from 1 to 9, especially from 3 to 6.

The compounds of formula I contain one or two asymmetric centers, i.e., two centers when $R_3$ is other than hydrogen. The compounds of formula I accordingly exist in stereomeric forms or as racemic mixtures thereof. All of these forms can be utilized in the method of this invention. The above described synthesis can utilize the starting compounds in the form of a racemic mixture or as a single isomer.

The compounds of formula I wherein $R_4$ is hydroxy form basic salts with a variety of inorganic or organic bases. The pharmaceutically acceptable salts of the compounds of formula I are useful within the method of this invention. Such pharmaceutically acceptable salts include alkali metal salts such as sodium or potassium, alkaline earth metal salts such as calcium or magnesium, and salts derived from amino acids such as arginine, lysine, etc. The salts are prepared by reacting the acid form of the compound, i.e., $R_4$ is hydroxy, with an equivalent of the base supplying the desired basic ion in a medium in which the salt precipitates or in aqueous medium and then lyophilizing.

Additionally, the compounds of formula I containing an amine group form acid-addition salts with a variety of inorganic and organic acids. The pharmaceutically acceptable salts include, for example, the hydrohalides, e.g., hydrochloride, hydrobromide, etc., sulfate, phosphate, nitrate, arylsulfonates, e.g., camphorsulfonate, benzenesulfonate, toluenesulfonate, etc., citrate, ascorbate, maleate, fumarate, pamoate, acetate, tartrate, salicylate and the like. It is frequently convenient to isolate the compound by forming the acid salt and precipitating in a medium in which it is insoluble. The bases also form quaternary ammonium salts with quaternizing agents which are acceptable for pharmaceutical use, e.g., lower alkyl halides such as methyl chloride, methyl bromide, ethyl chloride, etc., lower alkyl sulfates such as methyl sulfate, ethyl sulfates, etc., monocyclic aryl (lower alkyl) halides and sulfates such as benzyl chloride, benzyl sulfate, etc. This is accomplished by reacting the base with the alkyl halide, sulfate or the like.

The compounds of formula I when administered to a mammalian specie are useful analgesic agents due to their enkephalinase inhibition activity. While not limiting the scope of this invention to a specific theory or mechanism of action, it has been suggested that the endogenous opiate pentapeptides, [Met$^5$]-enkephalin (Tyr-Gly-Gly-Phe-Met) and [Leu$^5$]-enkephalin (Tyr-Gly-Gly-Phe-Leu), are neurotransmitters involved in central pain mediation (Hughes, et al., Nature, Vol. 258, December 1975, p. 577-579) and that these endogenous opioid peptides are functionally inactivated by cleavage of their Gly$^3$—Phe$^4$ peptide bonds by a specific peptidase, enkephalinase presumed to be specifically located at nerve terminals in the brain where enkephalins are released (Malfroy, et al., Nature, Vol. 276, November 1978, p. 523-526). Specific inhibitors of this enkephalinase enhance the recovery of endogenous enkephalins released from isolated brain slices (Patey, et al., Science, Vol. 212, June 1981, p 1153-1155) and cause analgesia in mice that is reversed by the opiate antagonist naloxone (Roques, et al., supra). In addition to analgesia, other pharmaceutical actions such as antitussive or antidiarrheal activities may result from prolonging the action of the body's natural opiates released from peripheral as well as central sites.

Thus, by the administration of a composition containing one or a combination of compounds of formula I or a pharmaceutically acceptable salt thereof, pain is alleviated in the mammalian host. A single dose, or preferably two to four divided daily doses, provided on a basis of about 0.1 to about 100 mg. per kilogram of body weight per day, preferably about 1 to about 25 mg. per kilogram per day, produces the desired analgesic activity. The composition is preferably administered orally but parenteral routes such as subcutaneous can also be employed.

In particular, it has been found that the compounds of formula I while possessing potent enkephalinase inhibition activity are far less active as angiotensin converting enzyme inhibitors than the corresponding α-amino acid compounds described above by Ondetti et al. and Greenberg, et al. Thus, administration of the compounds of formula I will produce a selective analgesic effect not possible with the α-amino acid compounds of the prior art.

The compounds of formula I can be utilized as enkephalinase inhibitors for the alleviation of pain by formulating in compositions such as tablets, capsules, or elixirs for oral administration or in sterile solutions or suspensions for parenteral administration. About 10 to 500 mg. of a compound or mixture of compounds of formula I or physiologically acceptable salt is compounded with a physiologically acceptable vehicle, carrier, excipient, binder, preservative, stabilizer, flavor, etc., in a unit dosage form as called for by accepted pharmaceutical practice. The amount of active substances in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples are illustrative of the invention. All temperatures are in degrees Celsius.

EXAMPLE 1

(±)-3-[[2-(Mercaptomethyl)-1-oxo-3-phenylpropyl-]amino]propanoic acid (a)

(±)-3-[[2-[(Acetylthio)methyl]-1-oxo-3-phenylpropyl-]amino]propanoic acid, ethyl ester A solution of (±)-2-[(acetylthio)methyl]-3-phenylpropanoic acid (0.95 g., 4.0 mmole) in ethyl ether (8 ml.) is treated, under a drying tube, with oxalyl chloride (0.37 ml., 4.2 mmole), followed cautiously with a catalytic amount of dimethylformamide (3 drops). The mixture is stirred for one hour at room temperature and then concentrated in vacuo. Tetrahydrofuran (5 ml.) is added to the residue and removed in vacuo to chase any remaining oxalyl chloride. The residue, a two-phase (yellow and green) liquid, is treated with methylene chloride (5 ml.), and the soluble portion is decanted into a dropping funnel. This solution is added dropwise, under nitrogen, to a cold (ice/methanol) mixture of β-alanine, ethyl ester, hydrochloride (0.61 g., 4.0 mmole) and diisopropylethylamine (1.46 ml., 8.38 mmole) in methylene chloride (10 ml.), over 10 minutes. After stirring for 3 hours the resulting slurry is filtered and concentrated. The residue is treated with ethyl acetate (50 ml.) and again filtered and the filtrate is washed with 10% potassium bisulfate, water, saturated sodium bicarbonate, and 50% brine (30 ml. each), then dried over Na$_2$SO$_4$ and concentrated in vacuo. The residue, a viscous yellow oil (1.20 g.), is purified on a column of 80 g. silica gel (230–400 mesh), eluting with 7:2 hexane/acetone. Fractions containing the desired product (TLC) are pooled and concentrated to give 1.04 g. of (±)-3-[[2-[(acetylthio)methyl]-1-oxo-3-phenylpropyl]amino]propanoic acid, ethyl ester as a clear almost colorless oil.

(b)

(±)-3-[[2-(Mercaptomethyl)-1-oxo-3-phenylpropyl]amino]propanoic acid

A solution of the product from part (a) (1.02 g., 3.02 mmole) in methanol (6 ml.) is chilled (ice/methanol) and to it, under nitrogen, is added 1N sodium hydroxide (6.35 ml.) over 15 minutes. The mixture is stirred for 3 hours while warming to room temperature (TLC indicates incomplete reaction), and additional 1N sodium hydroxide (3.0 ml.) is added in one portion. After stirring for an additional 3 hours at room temperature, the mixture is concentrated to approximately ½ volume in vacuo, and the residue is partitioned between water (50 ml.) and ethyl acetate (30 ml.). The aqueous layer is washed with ethyl acetate (30 ml.), adjusted to a pH of about 2 with concentrated hydrochloric acid, and extracted again with ethyl acetate (3×20 ml.). These organic layers are pooled, washed with water and brine (30 ml. each), dried (Na$_2$SO$_4$), and concentrated in vacuo to yield 0.71 g. of (±)-3-[[2-(mercaptomethyl)-1-oxo-3-phenylpropyl]amino]propanoic acid as a white solid; m.p. 76°–82°. TLC (silica gel, toluene/acetic acid; 4:1) R$_f$=0.37, minor spot at 0.07.

Anal. calc'd. for C$_{13}$H$_{17}$NO$_3$S: C, 58.40; H, 6.41; N, 5.24; S, 11.99. Found: C, 58.17; H, 6.34; N, 5.15; S, 11.85.

EXAMPLE 2

(±)-4-[[2-(Mercaptomethyl)-1-oxo-3-phenylpropyl]amino]butanoic acid (a) 4-Aminobutanoic acid, methyl ester, hydrochloride To a cold (−10°) suspension of 4-aminobutanoic acid (4.12 g., 40 mmole) in methanol (50 ml.), under nitrogen, is added, dropwise with mechanical stirring, thionyl chloride (5.86 ml., 80.0 mmole) at a rate so as to maintain the reaction temperature between −5° and −10°. The mixture is stirred overnight, warming to room temperature, and then is concentrated in vacuo. The off-white crystalline residue is triturated in ethyl ether (twice) and dried in vacuo to yield 6.25 g. of 4-aminobutanoic acid, methyl ester, hydrochloride as an almost white solid; m.p. 118.5°–122° (softens at 90°).

(b)

(±)-4-[[2-[(Acetylthio)methyl]-1-oxo-3-phenylpropyl]amino]butanoic acid, methyl ester Oxalyl chloride (0.37 ml., 4.2 mmole) is added, under nitrogen, to a solution of (±)-2-[(acetylthio)methyl]-3-phenylpropanoic acid (0.95 g., 4.0 mmol) in ethyl ether (8 ml.). This mixture is cautiously treated with a catalytic amount of dimethylformamide (3 drops), and then stirred for one hour at room temperature. After concentrating in vacuo, the residue is treated with tetrahydrofuran (10 ml.) and again concentrated to remove excess oxalyl chloride. The resulting residue is treated with methylene chloride (5 ml.), and the soluble portion is transferred to a dropping funnel. This solution is added, dropwise over 10 minutes, to a cold (−5°), stirred solution of 4-aminobutanoic acid, methyl ester, hydrochloride(0.68 g., 4.4 mmole) and diisopropylethylamine (1.6 ml., 9.0 mmole) in methylene chloride (10 ml.) under nitrogen. After stirring for 3 hours in the cold, the yellow solution is concentrated in vacuo. The residue is treated with ethyl acetate (60 ml.), filtered to remove diisopropylethylamine hydrochloride, and washed sequentially with 10% potassium bisulfate, water, 50% saturated sodium bicarbonate, and 50% brine (30 ml. each). The organic layer is dried (Na$_2$SO$_4$) and concentrated to a light brown solid (1.34 g.). This solid is adsorbed onto a small amount of silica gel (230–400 mesh), dried, and applied to column of 80 g. of the same silica. Elution with 5:2 hexane/acetone yields 1.09 g. of (±)-4-[[2-[(acetylthio)methyl]-1-oxo-3-phenylpropyl]amino]butanoic acid, methyl ester as a white solid; m.p. 81°–82°.

(c)

(±)-4-[[2-(Mercaptomethyl)-1-oxo-3-phenylpropyl]amino]butanoic acid

The product from part (b) (0.6 g., 1.8 mmole) is taken up in methanol (5 ml.) and chilled in an ice bath under nitrogen. 1N sodium hydroxide (5.4 ml., 3 equiv.) is added to this solution dropwise over 10 minutes. The mixture is stirred for 3 hours in the cold and then concentrated to approximately ½ volume in vacuo. The residue is diluted with water (40 ml.), washed with chloroform (2×15 ml.), and acidified to a pH of about 1.5 with concentrated hydrochloric acid. The resulting white suspension is extracted with ethyl acetate (3×15 ml.). These extracts are combined, washed with water and brine (15 ml. each), dried (Na$_2$SO$_4$) and concentrated to yield 0.48 g. of (±)-4-[[2-(mercaptomethyl)-1-oxo-3-phenylpropyl]amino]butanoic acid as a white solid; m.p. 94.5°–101°. TLC (silica gel, benzene/acetic acid; 4:1) R$_f$=0.41.

Anal. Calc'd. for C$_{14}$H$_{19}$NO$_3$S: C, 59.76; H, 6.81; N, 4.98; S, 11.40. Found: C, 59.81; H, 6.81; N, 4.96; S, 11.37.

EXAMPLE 3

(S)-3-[[2-(Mercaptomethyl)-1-oxo-3-phenylpropyl]amino]benzenebutanoic acid (Isomer A)

(a)

(S)-4-Phenyl-3-[[(phenylmethoxy)carbonyl]amino]butanoic acid, methyl ester (S)-[3-Diazo-2-oxo-1-(phenylmethyl)propyl]carbamic acid, phenylmethyl ester is prepared following the procedure described by Penka et al. (Helv. Chim. Acta, Vol. 53, p. 1057–1061, 1970), using isobutyl chloroformate in ethyl ether to form the mixed anhydride. Silver benzoate (1.0 g., 4.7 mmole) is mixed with triethylamine (10 ml.), and then filtered. An aliquot of the filtrate (approximately 0.5 ml.) is added to a solution of the diazo compound (2.0 g., 6.2 mmole) in methanol (20 ml.). Evolution of gas occurs and the mixture becomes dark. After bubbling ceases (approximately 10 minutes), the mixture is treated with additional silver benzoate solution (approximately 0.5 ml.), and stirred for 30 minutes. The mixture is then treated with activated charcoal, filtered, and concentrated in vacuo to a dark, tarry residue. Chromatography through Florisil (ethyl ether eluent) yields 1.65 g. of (S)-4-phenyl-3-[[(phenylmethoxy)carbonyl]amino]butanoic acid, methyl ester as a light yellow solid.

(b) (S)-3-Amino-4-phenylbutanoic acid, methyl ester, p-toluenesulfonic acid salt A solution of (S)-4-phenyl-3-[[(phenylmethoxy)carbonyl]amino]butanoic acid, methyl ester (1.64 g., 5.0 mmole) and p-toluenesulfonic acid monohydrate (0.95 g., 1.0 equiv.) in 95% ethanol (30 ml.) is treated, under argon, with 10% palladium/carbon catalyst (100 mg.). The mixture is stirred under a positive pressure of hydrogen for 1.5 hours, then filtered and concentrated to give an off-white residue. Recrystallization from acetonitrile (hot filtration) yields 1.44 g. of (S)-3-amino-4-phenylbutanoic acid, methyl ester, p-toluenesulfonic acid salt as needle-like white crystals; m.p. 168.5°–170.5°; $[\alpha]_D^{27} +7.0°$ (c=1.05, methanol).

(c)
(S)-3-[[2-[(Acetylthio)methyl]-1-oxo-3-phenylpropyl]amino]benzenebutanoic acid, methyl ester (isomer A)

Oxalyl chloride (1.1 equiv.) is added to a solution of (±)-2-[(acetylthio)methyl]-3-phenylpropanoic acid (0.92 g., 3.9 mmole) in ethyl ether (30 ml.) under argon. This solution is cautiously treated with dimethylformamide (2 drops) and allowed to stir for 45 minutes. The mixture is concentrated in vacuo and the residue is taken up in methylene chloride (5 ml.). This solution is added, dropwise over 10 minutes, to a cold (ice/methanol) solution of (S)-3-amino-4-phenylbutanoic acid, methyl ester, p-toluenesulfonic acid salt (1.41 g., 3.84 mmole) and diisopropylethylamine (1.35 ml., 7.75 mmole) in methylene chloride (20 ml.) under argon. The mixture is stirred for 3 hours, warming to room temperature, and then concentrated. The residue is partitioned between 50% saturated sodium bicarbonate (100 ml.) and ethyl acetate (3×30 ml.). The organic layers are combined, washed with water, 10% potassium bisulfate, and brine (50 ml. each), dried (Na$_2$SO$_4$), and concentrated to 1.57 g. of a slowly crystallizing yellow oil. This oil is applied to a column of 160 g. of silica gel (230–400 mesh) (preadsorbed on a small amount of the same gel) and eluted with 26% ethyl acetate/petroleum ether. Fractions containing only the faster moving isomer are combined and concentrated to yield 0.702 g. of (S)-3-[[2-[(acetylthio)methyl]-1-oxo-3-phenylpropyl]amino]benzenebutanoic acid, methyl ester (isomer A) as a white crystalline solid; m.p. 87°–88.5°; $[\alpha]_D^{26} -77.5°$ (c=0.96, chloroform).

(d)
(S)-3-[[2-(Mercaptomethyl)-1-oxo-3-phenylpropyl]amino]benzenebutanoic acid (isomer A)

A solution of the product from part (c) (0.35 g., 0.85 mmole) in methanol (2 ml.) is treated, under argon, with 1N sodium hydroxide (1.87 ml., 2.2 equiv.), dropwise over 10 minutes. After two hours, additional 1N sodium hydroxide (0.7 ml.) is introduced, and the mixture is treated with sufficient methanol to solubilize the precipitate. After stirring for 7 hours at room temperature, the methanol is evaporated off in vacuo. The residue is diluted with water and treated with 2N sodium hydroxide to solubilize the solids and then extracted with ethyl acetate (2×30 ml.) and hexane (30 ml.). The aqueous layer is acidified to a pH of about 1.0 with concentrated hydrochloric acid and extracted with ethyl acetate (3×20 ml.). These organic phases are combined, washed with water and brine (30 ml. each), dried (Na$_2$SO$_4$), and concentrated in vacuo to yield 0.23 g. of (S)-3-[[2-(mercaptomethyl)-1-oxo-3-phenylpropyl]amino]benzenebutanoic acid (isomer A) as white solids; m.p. 149°–151.5°; $[\alpha]_D^{26} +40.3°$ (c=1.00, methanol). TLC (silica gel, 7:1 benzene/acetic acid) R$_f$=0.40.

Anal. calc'd. for C$_{20}$H$_{23}$NO$_3$S: C, 67.20; H, 6.49; N, 3.92; S, 8.97. Found: C, 66.86; H, 6.45; N, 3.93; S, 8.71.

EXAMPLE 4

(S)-3-[[2-(Mercaptomethyl)-1-oxo-3-phenylpropyl]amino]benzenebutanoic acid (isomer B)

(a)
(S)-3-[[2-[(Acetylthio)methyl]-1-oxo-3-phenylpropyl]amino]benzenebutanoic acid, methyl ester (isomer B)

Following the procedure of Example 3 (c), fractions containing the slower isomer are pooled and concentrated to yield 0.67 g. of (S)-3-[[2-[(acetylthio)methyl]-1-oxo-3-phenylpropyl]amino]benzenebutanoic acid, methyl ester (isomer B) as a white solid; m.p. 93.5°–95°; $[\alpha]_D^{26} +55.4°$ (c=1.00, chloroform).

(b)
(S)-3-[[2-(Mercaptomethyl)-1-oxo-3-phenylpropyl]amino]benzenebutanoic acid (isomer B)

To a stirred solution of the product from part (a) (0.35 g., 0.85 mmole) in methanol (3 ml.) under argon there is added, dropwise over 15 minutes, a solution of sodium hydroxide (0.102 g., 3 equiv.) in 20% aqueous methanol (1.5 ml.). After stirring for 6 hours at room temperature, the reaction is incomplete (TLC) so an additional amount of sodium hydroxide (0.85 ml. of 1N aqueous sodium hydroxide) is introduced to the reaction mixture which is stored overnight in the cold (refrigerator). The next day, the methanol is removed in vacuo and the residue is partitioned between water (40 ml.) and ethyl acetate (2×25 ml.). The aqueous layer is acidified with concentrated hydrochloric acid to a pH of about 1.0 and then extracted with ethyl acetate (3×20 ml.). These extracts are combined, washed with water and brine (30 ml. each), dried (Na$_2$SO$_4$), and concentrated in vacuo to give 0.30 g. of (S)-3-[[2-(mercaptomethyl)-1-oxo-3-phenylpropyl]amino]benzenebutanoic acid (isomer B) as white solids; m.p. 148°–150°; $[\alpha]_D^{26} -28.9°$ (c=1.07, methanol). TLC (silica gel, 7:1 benzene/acetic acid) R$_f$=0.34.

Anal. calc'd. for C$_{20}$H$_{23}$NO$_3$S: C, 67.20; H, 6.49; N, 3.92; S, 8.97. Found: C, 66.95; H, 6.53; N, 3.82; S, 8.82.

EXAMPLE 5

(±)-5-[[2-(Mercaptomethyl)-1-oxo-3-phenylpropyl]amino]pentanoic acid (a) 5-Aminovaleric acid, methyl ester, hydrochloride Thionyl chloride (2.93 ml., 40 mmole) is added, dropwise with stirring, to a cold suspension of 5-aminovaleric acid (2.34 g., 20 mmole) in methanol (25 ml.) at a rate so as to maintain the reaction temperature between −5° and −10°. After the addition of the thionyl chloride is completed, the mixture is allowed to warm to room temperature and left to stir overnight. The mixture is concentrated in vacuo to give white crystals which are triturated in ether (twice) to give 2.86 g. of 5-aminovaleric acid, methyl ester, hydrochloride as white solids; m.p. 132°-137° (softens at 86°).

(b) (±)-5-[[2-[(Acetylthio)methyl]-1-oxo-3-phenylpropyl]amino]pentanoic acid, methyl ester Oxalyl chloride (0.45 ml., 5.2 mmole) is added to a solution of (±)-2-[(acetylthio)methyl]-3-phenylpropanoic acid (1.19 g., 5 mmole) in ethyl ether (10 ml.). This mixture is cautiously treated with a catalytic amount (3 drops) of dimethylformamide and then stirred for 1 hour at room temperature. The mixture is concentrated in vacuo, producing an oil which is dissolved in tetrahydrofuran (10 ml.) and again concentrated in vacuo. The resulting residue is dissolved in methylene chloride (6 ml.) and added dropwise over 10 minutes to a cold (−5°), stirred solution of 5-aminovaleric acid, methyl ester, hydrochloride (0.91 g., 5.4 mmole) and diisopropylethylamine (1.96 ml., 11.25 mmole) in methylene chloride (11 ml.). After stirring in the cold (−5°) for 2.5 hours the mixture is allowed to warm to room temperature and allowed to stir overnight. The next day, the mixture is concentrated in vacuo and the residue is taken up into ethyl acetate (60 ml.) and filtered to remove diisopropylethylamine hydrochloride. The filtrate is washed sequentially with 10% potassium bisulfate, water, 50% saturated sodium bicarbonate, and 50% brine (3×20 ml. each). The organic layer is dried (Na$_2$SO$_4$) and concentrated to give a very light yellow oil (1.40 g.). This oil is applied to a column of 115 g. of silica gel (230–400 mesh) and eluted with 5:2 hexane/acetone to yield 1.41 g. of (±)-5-[[2-[(acetylthio)methyl]-1-oxo-3-phenylpropyl]amino]pentanoic acid, methyl ester as a colorless oil.

(c) (±)-5-[[2-(Mercaptomethyl)-1-oxo-3-phenylpropyl]amino]pentanoic acid

1N Sodium hydroxide (12.9 ml., 3.8 equiv.) is added dropwise over 10 minutes to a chilled solution (ice bath) of the product from part (b) (1.20 g., 3.41 mmole) dissolved in methanol (13 ml.) under a nitrogen atmosphere. The mixture is stirred at 0° for 10 minutes and then allowed to warm to room temperature and stirred for 3 hours. The mixture is concentrated to half volume in vacuo. The residue is diluted with water (40 ml.) washed with chloroform (2×20 ml.), and acidified to a pH of about 1.5 with concentrated hydrochloric acid. The resulting white suspension is extracted with ethyl acetate (3×15 ml.). These organic extracts are combined, washed with water and brine (20 ml. each), dried (Na$_2$SO$_4$) and concentrated to yield a white waxy solid (0.82 g.). This solid is dissolved in ethyl acetate, filtered, concentrated and the residue triturated with ether to give (±)-5-[[2-(mercaptomethyl)-1-oxo-3-phenylpropyl]amino]pentanoic acid as white solids; m.p. 78°-79°. TLC (silica gel, 4:1 benzene/acetic acid) $R_f$=0.30 (slight tailing).

Anal. calc'd. for C$_{15}$H$_{21}$NO$_3$S: C, 60.99; H, 7.17; N, 4.74; S, 10.85. Found: C, 60.80; H, 7.15; N, 4.62; S, 10.73.

EXAMPLE 6
(±)-6-[[2-(Mercaptomethyl)-1-oxo-3-phenylpropyl]amino]hexanoic acid (a) 6-Aminocaproic acid, methyl ester, hydrochloride Thionyl chloride (2.93 ml., 40 mmole) is added dropwise with stirring to a cold suspension of 6-aminocaproic acid (2.62 g., 20 mmole) in methanol (25 ml.) at a rate so as to maintain the reaction temperature between −5° and −10°. After the addition of the thionyl chloride is completed, the mixture is allowed to warm to room temperature and allowed to stir for 4 hours. The mixture is then concentrated in vacuo to give a white solid which is triturated in ether (twice) to yield 3.53 g. of 6-aminocaproic acid, methyl ester, hydrochloride as white solids; m.p. 114°-118° (softens at greater than 109°).

(b) (±)-6-[[2-[(Acetylthio)methyl]-1-oxo-3-phenylpropyl]amino]hexanoic acid, methyl ester Oxalyl chloride (0.45 ml., 5.2 mmole) is added to a solution of (±)-2-[(acetylthio)methyl]-3-phenylpropanoic acid (1.19 g., 5 mmole) in ethyl ether (10 ml.). This mixture is cautiously treated with a catalytic amount (3 drops) of dimethylformamide and then stirred for one hour at room temperature. The mixture is concentrated in vacuo, producing an oil which is dissolved in tetrahydrofuran (10 ml.) and again concentrated in vacuo. The resulting residue is dissolved in methylene chloride (6 ml.) and added dropwise over 10 minutes to a cold (−5°), stirred solution of 6-aminocaproic acid, methyl ester, hydrochloride (0.98 g., 5.4 mmole) and diisopropylethylamine (1.96 ml., 11.25 mmole) in methylene chloride (11 ml.). After stirring in the cold (−5°) for 2.5 hours, the mixture is allowed to warm to room temperature and left to stir for 2 hours. The mixture is concentrated in vacuo and the residue taken up into ethyl acetate (60 ml.) and filtered to remove diisopropylethylamine hydrochloride. The filtrate is washed sequentially with 10% potassium bisulfate, water, 50% saturated sodium bicarbonate and 50% brine (3×20 ml. each). The organic layer is dried (Na$_2$SO$_4$) and concentrated to give 1.64 g. of (±)-6-[[2-[(acetylthio)methyl]-1-oxo-3-phenylpropyl]amino]hexanoic acid, methyl ester as a slightly yellow solid; m.p. 50°-54° (sinters at greater than 39°).

(c) (±)-6-[[2-(Mercaptomethyl)-1-oxo-3-phenylpropyl]amino]hexanoic acid

1N Sodium hydroxide (12 ml., 3 equiv.) is added, dropwise over 10 minutes, to a chilled solution (ice bath) of the product from part (b) (1.46 g., 3.99 mmole) dissolved in methanol (12 ml.) under a nitrogen atmosphere. The mixture is stirred at 0° for 10 minutes and then allowed to warm to room temperature and stirred for 3 hours. The mixture is concentrated to half volume in vacuo. The residue is diluted with water (40 ml.), washed with chloroform (2×20 ml.), and the aqueous portion is acidified to a pH of about 1.5 with concentrated hydrochloric acid. The resulting white suspension is extracted with ethyl acetate (3×15 ml.). These extracts are combined, washed with water and brine (20 ml. each), dried (Na$_2$SO$_4$) and concentrated to yield a colorless oil (1.23 g.). This oil is applied to a column of 80 g. of silica (230–400 mesh) and eluted with 20% acetic acid/toluene, yielding a colorless oil (0.99 g.). This oil is rechromatographed on 75 g. of silica (230–400 mesh) and eluted with 15% acetic acid/toluene to give a colorless oil (0.75 g.). This material is then applied to a column of silica AR cc-4 silica and eluted with chloroform, gradually adding ethyl acetate (10%–40% ethyl acetate) to yield a white solid (0.67 g.).

This solid is triturated with hexane/ether to give 0.456 g. of (±)-6-[[2-(mercaptomethyl)-1-oxo-3-phenylpropyl]amino]hexanoic acid as white solids; m.p. 58°–60°. TLC (silica, 4:1 toluene/acetic acid) $R_f=0.26$ (slight tailing).

Anal. calc'd. for $C_{16}H_{23}NO_3S \cdot 0.18H_2O$: C, 61.46; H, 7.53; N, 4.48; S, 10.25. Found: C, 61.46; H, 7.47; N, 4.40; S, 10.14.

EXAMPLE 7

(±)-5-[[2-(Mercaptomethyl)-1-oxo-3-phenylpropyl]amino]pentanoic acid, methyl ester (±)-5-[[2-[(Acetylthio)methyl]-1-oxo-3-phenylpropyl]amino]pentanoic acid, methyl ester (1.93 g., 5.5 mmole) is dissolved in methanol (10 ml.) and chilled in an ice bath under nitrogen. 1N Sodium hydroxide (5.5 ml., 1.0 eq.) is added to this solution dropwise over 10 minutes. The mixture is stirred at 0° for 10 minutes and then allowed to warm to room temperature and stirred for one hour. The mixture is concentrated to half volume in vacuo. The residue is diluted with water (20 ml.) and extracted with ethyl acetate (3×15 ml.). The organic layers are combined, washed with water and brine (15 ml. each), dried ($Na_2SO_4$), and concentrated to yield 1.68 g. of a colorless oil. This oil is applied to a column of about 125 g. Merck silica gel (230–400 mesh) and eluted with hexane/acetone (5:3) to yield 1.34 g. of (±)-5-[[2-(mercaptomethyl)-1-oxo-3-phenylpropyl]amino]pentanoic acid, methyl ester as a white solid; m.p. 39°–41°. TLC (silica gel, 5:3 hexane/acetone) $R_f=0.29$ (slight tailing).

Anal. calc'd. for $C_{16}H_{23}NO_3S$: C, 62.11; H, 7.49; N, 4.53; S, 10.36; SH, 10.69. Found: C, 61.86; H, 7.54; N, 4.50; S, 10.21; SH, 10.62.

EXAMPLE 8

(±)-7-[[2-[(Acetylthio)methyl]-1-oxo-3-phenylpropyl]amino]heptanoic acid, methyl ester (a) 7-Aminoheptanoic acid, methyl ester, hydrochloride (1:1)

Thionyl chloride (1.81 ml., 24.8 mmole) is added dropwise with stirring to a cold suspension of 7-aminoheptanoic acid (1.8 g., 12.4 mmole) in methanol (30 ml.) at a rate so as to maintain the reaction temperature between −5° and −10°. After addition of all the thionyl chloride, the mixture is allowed to warm to room temperature and is left to stir overnight. The mixture is then concentrated in vacuo to give a white solid which is triturated in ether (twice) to yield 2.38 g. of 7-aminoheptanoic acid, methyl ester, hydrochloride (1:1) as a white solid; m.p. 132°–134° (sinters above 118°).

(b)
(±)-7-[[2-[(Acetylthio)methyl]-1-oxo-3-phenylpropyl]amino]heptanoic acid, methyl ester Oxalyl chloride (0.67 ml., 7.69 mmole) is added to a solution of 3-acetylthio-2-benzylpropanoic acid (1.83 g., 7.67 mmole) in ethyl ether (15 ml.). This mixture is cautiously treated with a catalytic amount (2 drops) of dimethylformamide, and then stirred for one hour at room temperature. The mixture is concentrated in vacuo, producing an oil which is dissolved in tetrahydrofuran (15 ml.) and again concentrated in vacuo. The resulting residue is dissolved in methylene chloride (15 ml.) and added dropwise over 10 minutes to a cold (−5°), stirred solution of 7-aminoheptanoic acid, methyl ester, hydrochloride (1:1) (1.50 g., 7.67 mmole) and diisopropylethylamine (2.68 ml., 15.38 mmole) in methylene chloride (15 ml.). After stirring in the cold (−5°) for 2.5 hours, the mixture is allowed to warm to room temperature and left to stir overnight. The mixture is concentrated in vacuo and the residue is taken up into ethyl acetate (100 ml.) and filtered to remove diisopropylethylamine hydrochloride. The filtrate is washed sequentially with 10% potassium bisulfate, water, 5% saturated sodium bicarbonate, water, and 50% brine (3×30 ml. each). The organic layer is dried ($Na_2SO_4$) and concentrated to yield 2.60 g. of a white solid. This solid is recrystallized from hexane/ethyl acetate to yield 2.48 g. of (±)-7-[[2-[(acetylthio)methyl]-1-oxo-3-phenylpropyl]amino]heptanoic acid, methyl ester as a white solid, m.p. 84°–85° (sinters above 51°). TLC (silica gel, ethyl acetate/hexane 2:1) $R_f=0.45$.

Anal. calc'd. for $C_{20}H_{29}NO_4S$: C, 63.30; H, 7.70; N, 3.69; S, 8.45. Found: C, 63.01; H, 7.57; N, 3.51; S, 8.40.

EXAMPLE 9

(±)-7-[[2-(Mercaptomethyl)-1-oxo-3-phenylpropyl]amino]heptanoic acid (±)-7-[[2-[(Acetylthio)methyl]-1-oxo-3-phenylpropyl]amino]heptanoic acid, methyl ester (1.65 g., 4.3 mmole) is dissolved in methanol (20 ml.) by warming, and then chilled in an ice bath under nitrogen. 1N Sodium hydroxide (13 ml., about 3 eq.) is added dropwise over 10 minutes to this solution. The mixture is stirred at 0° for 10 minutes and then allowed to warm to room temperature and stirred for 3 hours. The mixture is concentrated in vacuo to remove all the methanol. The residue is diluted with water (40 ml.), washed with chloroform (2×20 ml.), and the aqueous portion is acidified to pH of about 1.5 with concentrated hydrochloric acid. The resulting white suspension is extracted with ethyl acetate (3×15 ml.). These extracts are combined, washed with water and brine (20 ml. each), dried ($Na_2SO_4$) and concentrated to yield 1.32 g. of a white solid. The solid is applied to a column of about 90 g. of Merck silica gel (230–400 mesh) and eluted with toluene/acetic acid (7:1) yielding 1.14 g. of a white solid. This material is then applied to a column of silica gel (SilicAR CC-4) and eluted with chloroform, gradually adding ethyl acetate (10% to 55% ethyl acetate) to yield 1.05 g. of (±)-7-[[2-(mercaptomethyl)-1-oxo-3-phenylpropyl]amino]heptanoic acid as a white solid; m.p. 71°–73° (sinters above 65°). TLC (silica gel, benzene/acetic acid 4:1) $R_f=0.36$ (trace at 0.27).

Anal. calc'd. for $C_{17}H_{25}NO_3S$: C, 63.13; H, 7.79; N, 4.30; S, 9.91; SH, 10.22. Found: C, 63.36; H, 7.91; N, 4.21; S, 9.57; SH, 9.89.

EXAMPLE 10

(±)-7-[[2-(Mercaptomethyl)-1-oxo-3-phenylpropyl]amino]heptanoic acid, methyl ester (±)-7-[[2-[(Acetylthio)methyl]-1-oxo-3-phenylpropyl]amino]heptanoic acid, methyl ester (1.43 g., 3.77 mmole) is dissolved in methanol (30 ml.) by warming, and then chilled in an ice bath under nitrogen. 1N Sodium hydroxide (3.77 ml., 1.0 eq.) is added dropwise over 10 minutes to this solution. The mixture is stirred at 0° for ten minutes and then allowed to warm to room temperature and stirred for one hour. The mixture is concentrated in vacuo to remove all the methanol. The residue is diluted with water (20 ml.) and extracted with ethyl acetate (3—15 ml.). These organic layers are combined, washed with water and brine (15 ml. each), dried (Na$_2$SO$_4$) and concentrated to yield 1.26 g. of a white solid. This solid is dissolved in 25 ml. of a 1:1 mixture of methanol:water and adjusted to pH of about 1.0 with concentrated hydrochloric acid. Zinc dust (80 mg.) is added to this solution and the mixture is stirred to room temperature for 30 minutes. The remaining zinc is filtered off and the filtrate is concentrated in vacuo to remove all the methanol. The residue is diluted with water (20 ml.) and then extracted with ethyl acetate (3×25 ml.). These organic layers are combined, washed with 5% sodium bicarbonate, water and brine (2×20 ml. each), dried (Na$_2$SO$_4$), and concentrated to yield 1.23 g. of a white solid. This material is purified by flash chromatography on 50 g. of Merck silica gel (230–400 mesh) eluting with ethyl acetate to yield 980 mg. of a white solid. This solid is taken up in methanol, filtered through a cellulose microfilter, and concentrated in vacuo to yield (±)-7-[[2-(mercaptomethyl)-1-oxo-3-phenylpropyl]amino]heptanoic acid, methyl ester, m.p. 68°–70°. TLC (silica gel, benzene/acetic acid 4:1) R$_f$=0.44.

Anal. calc'd. for C$_{18}$H$_{27}$NO$_3$S: C, 64.06; H, 8.06; N, 4.15; S, 9.50; SH, 9.80. Found: C, 64.33; H, 8.14; N, 3.99; S, 9.45; SH, 9.79.

EXAMPLE 11

(±)-8-[[2-(Mercaptomethyl)-1-oxo-3-phenylpropyl]amino]octanoic acid (a) 8-Aminooctanoic acid, methyl ester, hydrochloride (1:1)

Thionyl chloride (2.93 ml., 40 mmole) is added dropwise with stirring to a cold suspension of 8-aminooctanoic acid (3.18 g., 20 mmole) in methanol (25 ml.) at a rate so as to maintain the reaction temperature between −5° and −10°. After the addition of all of the thionyl chloride, the mixture is allowed to warm to room temperature and left to stir overnight. The mixture is concentrated in vacuo to give a white solid which is triturated in ether (twice) to yield 3.98 g. of 8-aminooctanoic acid, methyl ester, hydrochloride (1:1) as a white solid; m.p. 130°–132°.

(b) (±)-8-[[2-[(Acetylthio)methyl]-1-oxo-3-phenylpropyl]amino]octanoic acid, methyl ester Oxalyl chloride (0.45 ml., 5.2 mmole) is added to a solution of 3-acetylthio-2-benzylpropanoic acid (1.19 g., 5 mmole) in ethyl ether (10 ml.). This mixture is cautiously treated with a catalytic amount (3 drops) of dimethylformamide, and then stirred for one hour at room temperature. The mixture is concentrated in vacuo producing an oil which is dissolved in tetrahydrofuran (10 ml.) and again concentrated in vacuo. The resulting residue is dissolved in methylene chloride (6 ml.) and added dropwise over ten minutes to a cold (−5°), stirred solution of 8-aminooctanoic acid, methyl ester, hydrochloride (1:1) (1.06 g., 5.1 mmole) and diisopropylethylamine (1.96 ml., 11.25 mmole) in methylene chloride (11 ml.). After stirring in the cold (−5°) for 2.5 hours, the mixture is allowed to warm to room temperature and left to stir overnight. The mixture is then concentrated in vacuo and the residue is taken up into ethyl acetate (60 ml.) and filtered to remove diisopropylethylamine hydrochloride. The filtrate is washed sequentially with 10% potassium bisulfate, water, 5% saturated sodium bicarbonate, water and 50% brine (3×20 ml. each). The organic layer is dried (Na$_2$SO$_4$) and concentrated to yield 2.01 g. of a light yellow solid. This solid is dissolved in ethyl acetate and adsorbed onto a small amount of Merck silica (230–400 mesh). This material is then applied to a column of about 125 g. of the same silica and eluted with hexane/ethyl acetate (1:1) to yield 1.69 g. of (±)-8-[[2-[(acetylthio)methyl]-1-oxo-3-phenylpropyl]amino]octanoic acid, methyl ester as a white solid; m.p. 44°–45°.

(c) (±)-8-[[2-(Mercaptomethyl)-1-oxo-3-phenylpropyl]amino]octanoic acid

The methyl ester product from part (b) (1.69 g., 4.3 mmole) is dissolved in methanol (13 ml.) and chilled in an ice bath under nitrogen. 1N Sodium hydroxide (13 ml., about 3 eq.) is added dropwise over 10 minutes to this solution. The mixture is stirred at 0° for 10 minutes and then allowed to warm to room temperature and stirred for 4 hours. This solution is then flushed with argon and stored under refrigeration overnight. (A white precipitate forms after stirring for about 3.5 hours.) Methanol is added and the solution is concentrated in vacuo to remove all the methanol. The residue is diluted with water (40 ml.), washed with chloroform (2×20 ml.), and the aqueous portion is acidified to pH of about 1.5 with concentrated hydrochloric acid. The resulting white suspension is extracted with ethyl acetate (3×15 ml.). These extracts are combined, washed with water and brine (20 ml. each), dried (Na$_2$SO$_4$), and concentrated to yield 720 mg. of a white solid. The original chloroform layer is reextracted with 1N sodium hydroxide (2×15 ml.). The aqueous portion is acidified, combined with the previous acidified layer, and extracted with ethyl acetate (2×20 ml.). These extracts are washed with water and brine, dried and concentrated to yield an additional 380 mg. of white solid. The two portions of solid are combined to give 1.10 g of (±)-8-[[2-(mercaptomethyl)-1-oxo-3-phenylpropyl]amino]octanoic acid; m.p. 81°–83° (sinters above 68°). TLC (silica gel, benzene/acetic acid 4:1) R$_f$=0.42.

Anal. calc'd. for C$_{18}$H$_{27}$NO$_3$S: C, 64.06; H, 8.06; N, 4.15; S, 9.50; SH, 9.80. Found: C, 63.77; H, 7.84; N, 4.12; S, 9.18; SH, 9.66.

EXAMPLE 12

(±)-11-[[2-(Mercaptomethyl)-1-oxo-3-phenylpropyl]amino]undecanoic acid (a) 11-Aminoundecanoic acid, methyl ester, hydrochloride (1:1)

Thionyl chloride (5.84 ml., 80 mmole) is added dropwise with stirring to a cold suspension of 11-aminoundecanoic acid (8.05 g., 40 mmole) in methanol (50 ml.) at a rate so as to maintain the reaction temperature between −5° and −10°. After the addition of all of the thionyl chloride, the mixture is allowed to warm to room temperature. A white precipitate forms, which is dissolved by adding an additional 50 ml. of methanol to the mixture. The reaction is stirred at room temperature overnight. The mixture is concentrated in vacuo to give a white solid that is triturated in ether (twice) to yield 7.26 g. of 11-aminoundecanoic acid, methyl ester, hydrochloride (1:1); m.p. 155°–158°.

(b)
(±)-11-[[2-[(Acetylthio)methyl]-1-oxo-3-phenylpropyl]amino]undecanoic acid, methyl ester Oxalyl chloride (0.54 ml., 6.2 mmole) is added to a solution of 3-acetylthio-2-benzylpropanoic acid (1.43 g., 6 mmole) in ethyl ether (10 ml.). This mixture is cautiously treated with a catalytic amount (3 drops) of dimethylformamide, and then stirred for one hour at room temperature. The mixture is concentrated in vacuo producing an oil which is dissolved in tetrahydrofuran (10 ml.) and again concentrated in vacuo. The resulting residue is dissolved in methylene chloride (6 ml.) and added dropwise over ten minutes to a cold (−5°), stirred solution of 11-aminoundecanoic acid, methyl ester, hydrochloride (1:1) (1.61 g., 6.4 mmole) and diisopropylethylamine (2.23 ml., 12.8 mmole) in methylene chloride (11 ml.). After stirring in the cold (−5°) for 2.5 hours, the mixture is allowed to warm to room temperature and left to stir overnight. The mixture is then concentrated in vacuo and the residue is taken up into ethyl acetate (100 ml.) and filtered to remove diisopropylethylamine hydrochloride. The filtrate is washed sequentially with 10% potassium bisulfate, water, 5% sodium bicarbonate, water and 50% brine (3×30 ml. each). The organic layer is dried (Na$_2$SO$_4$) and concentrated to yield 2.5 g. of (±)-11-[[2-[(acetylthio)methyl]-1-oxo-3-phenylpropyl]amino]undecanoic acid, methyl ester as a light yellow solid; m.p. 64°–66°.

(c)
(±)-11-[[2-(Mercaptomethyl)-1-oxo-3-phenylpropyl]amino]undecanoic acid

The methyl ester product from part (b) (2.5 g., 5.74 mmole) is dissolved in methanol (25 ml.) and chilled in an ice bath under nitrogen. 1N Sodium hydroxide (23 ml., about 3 eq.) is added dropwise over 10 minutes to this solution. The solution becomes cloudy after addition of all the sodium hydroxide. The mixture is stirred at 0° for 10 minutes and then allowed to warm to room temperature and stirred for 3 hours. The mixture is concentrated in vacuo to remove all the methanol. The residue is diluted with water (40 ml.) and extracted with chloroform (2×20 ml.). The chloroform layer is extracted with 1N sodium hydroxide (3×20 ml.). All of the aqueous extracts are combined and acidified to a pH of about 1.5 with concentrated hydrochloric acid. The resulting white suspension is extracted with ethyl acetate (3×40 ml.). These extracts are combined, washed with water and brine (40 ml. each), dried (Na$_2$SO$_4$) and concentrated to yield 2.09 g. of a light yellow solid. This solid is recrystallized from a mixture of hexane, ethyl acetate, and ether to yield impure crystals. Therefore, the material is dissolved in ethyl acetate and adsorbed onto a small amount of silica gel (SilicAR CC-4), and applied to a column of the same silica. Elution with chloroform and gradual addition of ethyl acetate (10% to 40% ethyl acetate) yields 1.77 g. of (±)-11-[[2-(mercaptomethyl)-1-oxo-3-phenylpropyl]amino]undecanoic acid as a white solid; m.p. 104°–105°. TLC (silica gel, benzene/acetic acid 4:1) R$_f$=0.51.

Anal. calc'd. for C$_{21}$H$_{33}$NO$_3$S: C, 66.45; H, 8.76; N, 3.69; S, 8.45; SH, 8.71. Found: C, 66.12; H, 8.75; N, 3.65; S, 8.45; SH, 8.67.

EXAMPLE 13
(±)-5-[[2-(Mercaptomethyl)-1-oxo-3-phenylpropyl]amino]pentamide

(a) 5-[[(1,1-Dimethylethoxy)carbonyl]amino]pentanoic acid

Sodium hydroxide (1.0 g., 25 mmole) is added to a stirred solution of 5-aminopentanoic acid (2.93 g., 25 mmole) in 7.5 ml. of t-butanol:water (2:1). An additional 9 ml. of t-butanol:water (2:1) is added to effect dissolution, then di-t-butyl dicarbonate (6.0 g., 27.5 mmole) is added in several portions over a period of one hour. An additional 5 ml. of t-butanol is added and the thick white slurry is allowed to stir for 3.5 days. The reaction mixture is diluted with water (15 ml.) and extracted with hexane (3×15 ml.). The aqueous layer is acidified with potassium bisulfate (3.5 g. in 25 ml. of water). The product is extracted into ethyl acetate (1×25 ml., 2×15 ml.), washed with water and brine, dried (Na$_2$SO$_4$), and evaporated to yield 5.38 g. of a slowly crystallizing colorless oil. Trituration with hexane-ethyl ether gives 4.29 g. of 5-[[(1,1-dimethylethoxy)carbonyl]amino]pentanoic acid as a white crystalline solid; m.p. 47°–50.5°.

(b) 5-[[(1,1-Dimethylethoxy)carbonyl]amino]pentamide

Isobutyl chloroformate (1.55 ml., 12 mmole) in tetrahydrofuran (5 ml.) is added dropwise over approximately 5 minutes to a vigorously stirred solution of 5-[[(1,1-dimethylethoxy)carbonyl]amino]pentanoic acid (2.61 g., 12 mmole) and N-methylmorpholine (1.32 ml., 12 mmole) in tetrahydrofuran (15 ml.) at −15° while maintaining the reaction temperature between −25° and −15°. The reaction mixture is stirred for 12 minutes, then 10 ml. of a solution of ammonia in methanol (saturated at 0°) is added dropwise over 30 minutes at approximately −15°. The reaction mixture is stirred an additional 30 minutes in the cold, then allowed to warm to room temperature and left to stir overnight. The thick white suspension is diluted with water, concentrated in vacuo to remove organic solvents and then extracted with ethyl acetate (150 ml.). The ethyl acetate solution is washed with water, 10% potassium bisulfate, water and brine, dried (Na$_2$SO$_4$), and evaporated to give 1.54 g. of white solid product; m.p. 135°–138.5°.

Since the recovery is low, the initial aqueous extract is concentrated to half volume and extracted with ethyl acetate (1×75 ml., 3×25 ml.). The ethyl acetate solution is washed with water (2×10 ml.) and brine (2×10 ml.) dried (Na$_2$SO$_4$) and concentrated to yield 0.56 g. of white solid, bringing the total yield up to 2.1 g. A small portion is recrystallized from ethyl acetate to yield an analytically pure sample of 5-[[(1,1-dimethylethoxy)carbonyl]amino]pentamide; m.p. 138°–140°.

(c) 5-Aminopentamide, hydrochloride (1:1)

A solution of 5-[[(1,1-dimethylethoxy)carbonyl]amino]pentamide (1.77 g., 8.18 mmole) in 20 ml. of 1.3N hydrogen chloride in acetic acid is allowed to stand at room temperature for 45 minutes. The solvent is evaporated under reduced pressure and the oily residue is triturated with cold ethyl ether to produce a hard gum. Addition of approximately 2 ml. of methanol allows the product to be triturated to a fine white powder, which is collected, yielding 1.18 g. of of 5-aminopentamide, hydrochloride (1:1).

(d) (±)-5-[[2-[(Acetylthio)methyl]-1-oxo-3-phenylpropyl]amino]pentamide

To a solution of 3-acetylthio-2-benzylpropanoic acid (1.43 g., 6 mmole) and oxalyl chloride (0.58 ml., 6.6 mmole) in ethyl ether (12 ml.) is added one drop of dimethylformamide. The reaction mixture is allowed to stir for one hour at room temperature, then concentrated in vacuo. The residue is twice taken up into tetrahydrofuran (5-10 ml.) and evaporated to remove the last traces of oxalyl chloride, and then evacuated on the vacuum pump for 10 minutes. A solution of this acid chloride in 7.5 ml. of methylene chloride is added dropwise over one hour at 5°-10° to a solution of 5-aminopentamide, hydrochloride (1:1) (916 mg., 6 mmole) and diisopropylethylamine (2.09 ml., 12 mmole) in 15 ml. of methylene chloride. The reaction mixture is stirred for one hour in the cold, then allowed to warm to room temperature and stirred for 2 hours. The solvent is evaporated and the residue is taken up into ethyl acetate (200 ml.), washed sequentially with water, 5% sodium bicarbonate, water, 10% potassium bisulfate, water and brine (approximately 2×20 ml. each), dried (Na$_2$SO$_4$) and concentrated in vacuo to give 1.44 g. of a white solid. Two recrystallizations from ethyl acetate-hexane yield 0.86 g. of (±)-5-[[2-[(acetylthio)methyl]-1-oxo-3-phenylpropyl]amino]pentamide.

(e) (±)-5-[[2-(Mercaptomethyl)-1-oxo-3-phenylpropyl]amino]pentamide

1N Sodium hydroxide (2.53 ml., 1 eq.) is added dropwise over 5 minutes to a solution of (±)-5-[[2-[(acetylthio)methyl]-1-oxo-3-phenylpropyl]amino]pentamide (0.85 g., 2.53 mmole) in 5 ml. of methanol at 0°-5°. The ice bath is removed and the reaction mixture is stirred for 1.5 hours. Most of the methanol is evaporated and the residue is then diluted with water (about 7 ml.) and adjusted to pH 7.0 with 1N hydrochloric acid. The solid which separates is extracted into ethyl acetate (10 ml., then 3×20 ml.). The combined organic extract is washed with brine, dried (Na$_2$SO$_4$), and concentrated in vacuo to give 0.75 g. of a white solid residue; m.p. 112°-122°. One recrystallization from methanol-water gives material with m.p. 122.5°-125°. The solid and mother liquor are recombined and concentrated, then applied to a column of silica gel (silicAR CC-4) packed in chloroform. The column is eluted initially with 10% ethyl acetate in chloroform, gradually increasing the eluent polarity to ethyl acetate and finally 10% methanol in ethyl acetate to yield 0.50 g. of (±)-5-[[2-(mercaptomethyl)-1-oxo-3-phenylpropyl]amino]pentamide as a white solid; m.p. 127°-128.5°. TLC (silica gel; benzene/acetic acid, 7:3) R$_f$=0.25 with faint tailing.

Anal. calc'd. for C$_{15}$H$_{22}$N$_2$O$_2$S: C, 61.19; H, 7.53; N, 9.51; S, 10.89; SH, 11.23. Found: C, 60.88; H, 7.64; N, 9.28; S, 10.83; SH, 11.11.

EXAMPLES 14–45

Following the procedure of Examples 1 to 13 but employing the amino compound shown in Col. I and the carboxylic acid shown in Col. II one obtains the acylmercaptoalkanoyl compound shown in Col. III. Hydrolysis yields the mercaptoalkanoyl compound shown in Col. IV.

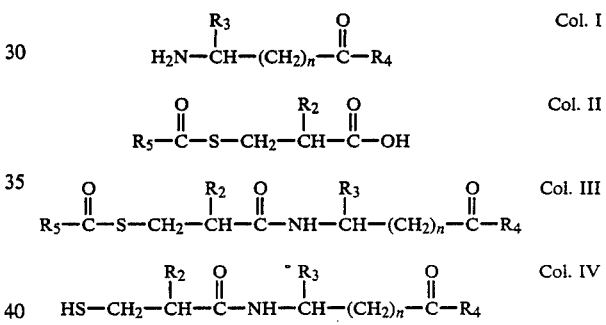

| Example | R₃ | n | R₄ | R₂ | R₅ |
|---|---|---|---|---|---|
| 14 | —H | 15 | —OCH₃ | —CH₂—(phenyl) | —CH₃ |
| 15 | —H | 7 | —OCH₃ | —CH₂—(phenyl) | —CH₃ |
| 16 | —H | 8 | —OCH₃ | —CH₂—(phenyl) | —CH₃ |
| 17 | —CH₃ | 2 | —OC₂H₅ | —CH₂—(thienyl, S) | —(phenyl) |
| 18 | —CH₂CH(CH₃)₂ | 3 | —OCH₃ | —CH₂—(thienyl, S) | —(phenyl) |
| 19 | —(CH₂)₃CH₃ | 4 | —OCH₃ | —CH₂—(furyl, O) | —CH₃ |
| 20 | —CH₂—(phenyl) | 5 | —OCH₃ | —CH₂—(pyridyl, N) | —CH₃ |
| 21 | —(CH₂)₂—(phenyl) | 3 | —OCH₃ | —CH₂—(indolyl, N—H) | —CH₃ |

-continued

| Example | R₁ | n | R₄ | R₂ | R₃ |
|---|---|---|---|---|---|
| 22 | phenyl | 6 | —OC₂H₅ | —CH₂-imidazole (CH₂ linked to N–H, N=CH) | —CH₃ |
| 23 | 4-methoxybenzyl (—CH₂—C₆H₄—OCH₃) | 2 | —OCH₃ | —CH₃ | —CH₃ |
| 24 | —H | 7 | —OCH₃ | —(CH₂)₂—C₆H₅ | —CH₃ |
| 25 | —H | 8 | —OCH₃ | —(CH₂)—C₆H₄—CH₃ (4-) | —CH₃ |
| 26 | —CH₂—C₆H₅ | 4 | —OCH₃ | —(CH₂)—C₆H₄—Cl (4-) | —CH₃ |
| 27 | —CH₂—(2-thienyl) | 3 | —OCH₃ | —(CH₂)₃—C₆H₅ | —CH₃ |
| 28 | —CH₂—(2-furyl) | 4 | —OCH₃ | —(CH₂)₄—C₆H₅ | —CH₃ |
| 29 | —(CH₂)₂—(3-pyridyl) | 2 | —OCH₃ | —CH₂—C₆H₅ | —CH₂—C₆H₅ |

-continued

| Example | R₃ | n | R₄ | R₂ | R₅ |
|---|---|---|---|---|---|
| 30 | −CH₂−CH=CH−NH (imidazole-like) | 3 | −OCH₃ | −CH₂−(phenyl) | 4-pyridyl |
| 31 | −CH₂−(indole) | 4 | −OC₂H₅ | −CH₂−(phenyl) | phenyl |
| 32 | −(CH₂)₂−(thiophene) | 2 | −OC₃H₇ | phenyl | −CH₃ |
| 33 | −H | 5 | −OCH₃ | 4-(PhO−CH₂−)−C₆H₄−CH₂− | −CH₃ |
| 34 | −CH₂−(phenyl) | 4 | −OCH₃ | −CH₂−(phenyl) | 2-(CH₂−)thiophene |
| 35 | −H | 2 | −O−CH₂−CH₂−N(CH₃)₂ | −CH₂−(phenyl) | −CH₃ |
| 36 | −H | 3 | CH₃−NH− | −CH₂−(phenyl) | −CH₃ |
| 37 | −CH₂−(phenyl) | 3 | −N(CH₃)₂ | −CH₂−(phenyl) | −CH₃ |

-continued

| Example | R₃ | n | R₄ | R₂ | R₅ |
|---|---|---|---|---|---|
| 38 | —H | 4 | —O—CH₂—C₆H₅ | —CH₂—C₆H₅ | —C₆H₅ |
| 39 | —H | 5 | —CH₂—N(H)—C₆H₅ | —CH₂—C₆H₄—NO₂ | —CH₃ |
| 40 | —CH₃ | 6 | —CH₂—N(CH₃)—C₆H₅ | —CH₂—(4-pyridyl) | —CH₃ |
| 41 | —H | 4 | —N(C₂H₅)₂ | —CH₂—(3-pyridyl) | —C₆H₅ |
| 42 | —H | 3 | 4-methylpiperazin-1-yl | —CH₂—C₆H₅ | —CH₃ |
| 43 | —H | 5 | —OCH₃ | —CH₂—C₆H₅ | —CH₃ |
| 44 | —H | 3 | —OCH₃ | —CH₂—C₆H₅ | —CH₃ |
| 45 | —CH₂—C₆H₅ | 4 | —OCH₃ | —CH₂—C₆H₄—NH—C(O)—OC(CH₃)₃ | —CH₃ |

In the case of Examples 14 to 35, 38 and 43 to 45 hydrolysis of the acylmercaptoalkanoyl ester wil yield depending upon the conditions employed either the corresponding mercaptoalkanoyl carboxylic acid, i.e., $R_4$ is hydroxy, or the corresponding mercaptoalkanoyl carboxylic acid ester, i.e., $R_4$ is as in column III. The hydroxy protecting group in Example 33 and the amino protecting group shown in Example 45 would be removed following completion of the reaction.

EXAMPLE 46

(±)-5-[[2-(Mercaptomethyl)-1-oxo-3-phenylpropyl-]amino]pentanoic acid, sodium salt (±)-5-[[2-(Mercaptomethyl)-1-oxo-3-phenylpropyl-]amino]pentanoic acid (1 mmole) is dissolved in water (50 ml.). Aqueous sodium bicarbonate (0.1N, 20 ml.) is added and the aqueous solution is lyophilized. It is then dissolved in water (10 ml.) and applied on a column (5 cm×60 cm) of Sephadex chromatography gel G-10 and eluted with water. Fractions containing the desired product are pooled and lyophilized to give (±)-5-[[2-(mercaptomethyl)-1-oxo-3-phenylpropyl]amino]pentanoic acid, sodium salt.

EXAMPLE 47

1000 tablets each containing 100 mg. of (±)-5-[[2-(mercaptomethyl)-1-oxo-3-phenylpropyl]amino]pentanoic acid are produced from the following ingredients:

| | |
|---|---|
| (±)-5-[[2-(Mercaptomethyl)-1-oxo-3-phenylpropyl]amino]-pentanoic acid | 100 g. |
| Corn starch | 50 g. |
| Gelatin | 7.5 g. |
| Avicel (Microcrystalline cellulose) | 25 g. |
| Magnesium stearate | 2.5 g. |

The (±)-5-[[2-(mercaptomethyl)-1-oxo-3-phenylpropyl]amino]pentanoic acid and corn starch are admixed with an aqueous solution of the gelatin. The mixture is dried and ground to a fine powder. The Avicel and then the magnesium stearate are admixed with the granules. This mixture is then compressed in a tablet press to form 1000 tablets each containing 100 mg. of active ingredient.

The compounds of Examples 1 to 4 and 6 to 45 can be formulated in a similar manner.

What is claimed is:

1. A compound of the formula:

$$R_5-\overset{O}{\overset{\|}{C}}-S-CH_2-\overset{R_2}{\underset{|}{CH}}-\overset{O}{\overset{\|}{C}}-NH-\overset{R_3}{\underset{|}{CH}}-(CH_2)_n-\overset{O}{\overset{\|}{C}}-R_4$$

including a pharmaceutically acceptable salt thereof wherein:

$R_2$ is —(CH$_2$)$_m$—⟨phenyl⟩ or —(CH$_2$)$_m$—⟨phenyl-(R$_6$)$_r$⟩;

$R_3$ is hydrogen, lower alkyl,

—(CH$_2$)$_m$—⟨phenyl⟩, —(CH$_2$)$_m$—⟨phenyl-(R$_6$)$_r$⟩;

$R_4$ is —OH or —OCH$_3$;

n is an integer from 1 to 15;

$R_5$ is lower alkyl,

—(CH$_2$)$_m$—⟨phenyl⟩, or —(CH$_2$)$_m$—⟨phenyl-(R$_6$)$_r$⟩;

m is zero or an integer from 1 to 4;

$R_6$ is lower alkyl of 1 to 4 carbons, lower alkoxy of 1 to 4 carbons, lower alkylthio of 1 to 4 carbons, hydroxy, Cl, Br, F or trifluoromethyl; and r is an integer from 1 to 3 provided that r is more than one only if $R_6$ is hydroxy, methyl, methoxy, Cl, or F.

2. A compound of claim 1 wherein:

$R_1$ is $$H_3C-\overset{O}{\overset{\|}{C}}- \quad \text{or} \quad \text{⟨phenyl⟩}-\overset{O}{\overset{\|}{C}}-;$$

$R_2$ is

—(CH$_2$)$_m$—⟨phenyl⟩ or —(CH$_2$)$_m$—⟨phenyl-R$_6$⟩;

$R_3$ is hydrogen, straight or branched chain alkyl of 1 to 4 carbons,

—(CH$_2$)$_m$—⟨phenyl⟩, or —(CH$_2$)$_m$—⟨phenyl-R$_6$⟩;

m is one or two;

$R_6$ is methyl, methoxy, Cl, F, or hydroxy; and n is an integer from 1 to 9.

3. A compound of claim 2 wherein:
$R_2$ is benzyl; and
n is an integer from 3 to 6.

4. A compound of claim 2 wherein $R_1$ is $$H_3C-\overset{O}{\overset{\|}{C}}-.$$

5. A compound of claim 3 wherein $R_1$ is $$H_3C-\overset{O}{\overset{\|}{C}}-.$$

6. A compound of claim 2 wherein R₁ is

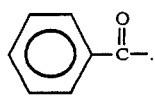

7. The compound of claim 3 wherein R₁ is

8. A compound of claim 5 wherein n is 3.
9. The compound of claim 8 wherein R₃ is hydrogen; and
R₄ is —OCH₃.
10. A compound of claim 5 wherein n is 4.
11. A compound of claim 5 wherein n is 5.
12. The compound of claim 11 wherein R₃ is hydrogen; and
R₄ is —OCH₃.
13. A compound of claim 5 wherein n is 6.
14. A compound of claim 7 wherein n is 3.
15. A compound of claim 7 wherein n is 4.
16. A compound of claim 7 wherein n is 5.
17. A compound of claim 7 wherein n is 6.

* * * * *